(12) United States Patent
Mohr et al.

(10) Patent No.: US 10,314,782 B2
(45) Date of Patent: *Jun. 11, 2019

(54) ORAL SUSPENSION COMPRISING TELMISARTAN

(71) Applicants: Detlef Mohr, Biberarch an der Riss (DE); Stefan Lehner, Wiesbaden (DE)

(72) Inventors: Detlef Mohr, Biberarch an der Riss (DE); Stefan Lehner, Wiesbaden (DE)

(73) Assignee: BOEHRINGER INGELHEIM VETMEDICA GMBH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/469,750

(22) Filed: Aug. 27, 2014

(65) Prior Publication Data

US 2014/0364473 A1 Dec. 11, 2014

Related U.S. Application Data

(63) Continuation of application No. 13/321,216, filed as application No. PCT/EP2010/056895 on May 19, 2010, now Pat. No. 8,871,795.

(30) Foreign Application Priority Data

May 20, 2009 (EP) .................................. 09160771

(51) Int. Cl.
| | | |
|---|---|---|
| *A61K 31/4184* | (2006.01) | |
| *A61K 9/08* | (2006.01) | |
| *A61K 47/26* | (2006.01) | |
| *A61P 9/12* | (2006.01) | |
| *A61K 9/00* | (2006.01) | |
| *A61K 47/10* | (2017.01) | |

(52) U.S. Cl.
CPC .............. *A61K 9/0095* (2013.01); *A61K 9/08* (2013.01); *A61K 31/4184* (2013.01); *A61K 47/10* (2013.01); *A61K 47/26* (2013.01)

(58) Field of Classification Search
CPC ... A61K 9/0095; A61K 31/4184; A61K 47/26
USPC ........................................... 424/400; 514/394
See application file for complete search history.

(56) References Cited

U.S. PATENT DOCUMENTS

| | | | | |
|---|---|---|---|---|
| 4,448,778 A * | 5/1984 | Lynch | ...................... | A23G 3/38 426/573 |
| 4,880,804 A | 11/1989 | Carini et al. | | |
| 5,591,762 A * | 1/1997 | Hauel | .................. | A61K 31/415 514/222.2 |
| 5,846,962 A | 12/1998 | Suzuki et al. | | |
| 6,028,091 A | 2/2000 | Hill | | |
| 6,204,281 B1 | 3/2001 | Webb et al. | | |
| 6,358,986 B1 | 3/2002 | Schneider | | |
| 6,410,742 B1 | 6/2002 | Schneider | | |
| 6,589,547 B1 | 7/2003 | Igari et al. | | |
| 6,737,432 B2 | 5/2004 | Donsbach et al. | | |
| 8,871,795 B2 * | 10/2014 | Mohr | .................. | A61K 9/0095 424/400 |
| 2002/0094997 A1 | 7/2002 | Schneider et al. | | |
| 2004/0033258 A1 | 2/2004 | Koike | | |
| 2004/0110813 A1 | 6/2004 | Nakatani et al. | | |
| 2004/0219208 A1 | 11/2004 | Kawamura et al. | | |
| 2005/0070594 A1 | 3/2005 | Kauschke et al. | | |
| 2005/0186274 A1 | 8/2005 | Kohlrausch | | |
| 2005/0272649 A1 | 12/2005 | Hruska et al. | | |
| 2007/0026026 A1 | 2/2007 | Delmarre et al. | | |
| 2007/0155679 A1 | 7/2007 | Daemmgen et al. | | |
| 2008/0146543 A1 | 6/2008 | Stark et al. | | |
| 2012/0095069 A1 | 4/2012 | Mohr et al. | | |

FOREIGN PATENT DOCUMENTS

| | | |
|---|---|---|
| CA | 2352436 A1 | 7/2000 |
| CN | 1765362 A | 5/2006 |
| DE | 1023027 B | 1/1958 |
| DE | 10335027 A1 | 2/2005 |
| EP | 1579862 A1 | 9/2005 |
| EP | 2420232 A2 | 2/2012 |
| JP | H11315034 A | 11/1999 |
| WO | 1996031234 A1 | 10/1996 |
| WO | 1997049392 A1 | 12/1997 |
| WO | 1999044590 A1 | 9/1999 |
| WO | 2000043370 A1 | 7/2000 |
| WO | 2001078699 A2 | 10/2001 |
| WO | 2003037876 A1 | 5/2003 |
| WO | 2004014308 A2 | 2/2004 |
| WO | 2004028505 A1 | 4/2004 |
| WO | 2005070463 A2 | 8/2005 |
| WO | 2005123070 A1 | 12/2005 |
| WO | 2006048208 A1 | 5/2006 |
| WO | 2008040774 A2 | 4/2008 |
| WO | 2008110599 A1 | 9/2008 |

(Continued)

OTHER PUBLICATIONS

Maltitol JEFCA 1996, published in FNP 52 Add 4 (1996).*
Lactitol JEFCA 1996, published in FNP 52 Add 4 (1996).*
Grauer, Gregory, "ACE Inhibitors and CKD", 2 pages. [Accessed at : http://www.dvm360storage.com/cvc/proceedings/dc/Urology/Grauer/Grauer,Gregory_ACE_Inhibitors_and_CKD.pdf on Feb. 5, 2015].
Syme et al., "Survival of Cats with Naturally Occurring Chronic Renal Failure Is Related to Severity of Proteinuria". Journal of Veterinary Internal Medicine, vol. 20, No. 3, 2006, pp. 528-535.
Abstract in English of JPH11315034, 1999.
Guangxi Agricultural College et al., "Oxidation in acidic solutions". Organic Chemistry, Guangxi People's Publishing House, Dec. 1982, p. 235.

(Continued)

*Primary Examiner* — Irina Neagu
(74) *Attorney, Agent, or Firm* — Judy Jarecki-Black

(57) ABSTRACT

A pharmaceutical solution with a pH value of 10 or higher contains an angiotensin II receptor antagonist, where one or more sugar alcohols are present up to a total concentration of 40 wt. % to 70 wt. %.

11 Claims, No Drawings

(56) References Cited

FOREIGN PATENT DOCUMENTS

WO         2010133638 A1    11/2010

OTHER PUBLICATIONS

Hiwada, Kunio, "Presentation of New Drug: Telmisartan". Vascular Biology & Medicine, vol. 3, No. 5, 2002, pp. 571-576.
Ono et al., "Characteristics of the Long-Acting Sartan Telmisartan". Circulation Control, vol. 23, No. 4, 2002, pp. 462-466.
Abstract in English of CN1765362, 2006.
Allen, Andrew L., "The Diagnosis of Acetaminophen toxicosis in cats"., The Canadian Veterinary Journal, vol. 44, No. 6, Jun. 2003, pp. 509-510.
Asiedu-Gyekye et al. "Does losartan prevent cerebral edema? A preliminary study using a vascular compartment model". Medical Science Monitor, vol. 9, No. 3, Mar. 2003, pp. BR127-BR130.
Berny et al., "Animal Poisoning in Europe. Part 2: Companion Animals". The Veterinary Journal, vol. 183, 2010, pp. 255-259.
Burnier et al., "Angiotensin II receptor antagonists". The Lancet, vol. 355, 2000, pp. 637-645.
Champion et al., "Analysis of the Effects of Candesartan on Responses to Angiotensin II in the Hindquarters Vascular Bed of the Cat". Journal of the American Society of Nephrology, vol. 10, 1999, pp. S101-S103.
Cingolani et al., "The Positive Inotropic Effect of Angiotensin II: Role of Endothelin-1 and Reactive Oxygen Species". Hypertension, vol. 47, No. 4, Apr. 2006, pp. 727-734.
Conlon, Peter D., "Nonsteroidal Drugs Used in the Treatment of Inflammation". Clinical Pharmacology, vol. 18, No. 6, 1988, pp. 1115-1131.
Coronel et al., "Hypertension Treatment in Nondiabetic Advanced Chronic Kidney Disease Patients with Irbesartan. Effect on Serum Uric Acid". Abstract, Journal of Hypertension, vol. 23, Supp. 2, 2005, p. S65.
Court et al., "Molecular Basis for Deficient Acetaminophen Glucuronidation in Cats an Interspecies Comparison of Enzyme Kinetics in Liver Microsomes," 1997, Biochemical Pharmacology, vol. 53, pp. 1041-1047.
Ebner et al., "Disposition and Chemical Stability of Telmisartan 1-O-acylglucuronide". 1999, The American Society for Pharmacology & Experimental Therapeutics, vol. 27, No. 10, pp. 1143-1149.
Ettinger et al., "Therapeutic Considerations in Medicine and Disease", Textbook of Veterinary Internal Medicine Diseases of the Dog and Cat, Sixth Edition, vol. 1, Section VI, Table 143, 2005, pp. 530-531.
Garrison et al., "[Pro11, D-Ala12] angiotensin I has rapid onset vasoconstrictor activity in the cat". American Journal of Physiology-Endocrinology and Metabolism, vol. 273, No. 6, 1997, pp. E1059-E1064.
Huskey et al., "N-glucuronidation reactions. I. Tetrazole N-glucuronidation of selected angiotensin II receptor antagonists in hepatic microsomes from rats, dogs, monkeys, and humans." Abstract, Drug Metabolism and Disposition, vol. 21, No. 5, 1993, pp. 792-299 (p. A-9).
Iino et al., "Renoprotective Effect of Losartan in Comparison to Amlodipine in Patients with Chronic Kidney Disease and Hypertension—a Report of the Japanese Losartan Therapy Intended for the Global Reneal Protection in Hypertensive Patients (JLIGHT) Study". Hypertension Research, vol. 27, No. 1, 2004, pp. 21-30.
International Search Report for PCT/EP2010/056895 dated Aug. 3, 2010.
Israili, Z.H., "Clinical pharmacokinetics of angiotensin II (AT1) receptor blockers in hypertension". Journal of Human Hypertension, vol. 14, Suppl. 1, 2000, pp. S73-S86.
Kemper et al., "Metabolism: A Determinant of Toxicology". Principles and Methods of Toxicology, 5th Edition, Chapter 3, Informa Healthcare USA, New York, NY, 2008, pp. 139-142.
Koide et al., "Hypertrophic response to hemodynamic overload: role of load vs. renin-angiotensin system activation". American Journal of Physiology—Heart, vol. 276, 1999, pp. H350-H358.
Kondo et al., "Characterization of conjugated metabolites of a new angiotensin II receptor antagonist, candesartan cilexetil, in rats by liquid chromatography/electrospray tandem mass spectrometry following chemical derivatization." Abstract, Journal of Mass Spectrometry, vol. 31, No. 8, Aug. 1996, pp. 873-878 (p. A-11).
Kumari et al., "Effect of Pre- and Posttreatment of Losartan in Feline Model of Myocardial Ischemic-Reperfusion Injury". Methods and Findings in Experimental and Clinical Pharmacology, vol. 26, No. 1, 2004, pp. 39-45.
Lazaro et al., "Forum Original Research Communication: Long-Term Blood Pressure Control Prevents Oxidative Renal Injury." Antioxidants & Redox Signaling, vol. 7, Nos. 9 & 10, 2005, pp. 1285-1293.
Lefebvre et al., "Angiotensin-converting enzyme inhibitors in the therapy of renal diseases". Journal of Veterinary Pharmacology and Therapeutics, vol. 27, 2004, pp. 265-281.
Malike et al., "Permethrin Spot on Intoxication of Cats: Literature review and survey of veterinary practioners in Australia". Journal of Feline Medicine and Surgery, vol. 12, 2010, pp. 5-14.
Mathur et al., "Evaluation of a technique of inducing hypertensive renal insufficiency in cats". American Journal of Veterinary Research, vol. 65, No. 7, Jul. 2004, pp. 1006-1013.
Osweiler, Gary D., "Toxicological Concepts: Factors that Influence Toxicology", General Toxicological Principles, in Small Animal Toxicology, Elsevier, Inc., St. Louis, MO, 2006, p. A17.
Perrier et al., "In vitro N-glucuronidation of SB 47436 (BMS 186295), a new AT1 nonpeptide angiotensin II receptor antagonist, by rat, monkey and human hepatic microsomal fractions." Abstract, The Journal of Pharmacology and Experimental Therapeutics, vol. 271, No. 1, Oct. 1994, pp. 91-99 (p. A-10).
Rodriguez-Iturbe et al., "Early treatment with cGMP phosphodiesterase inhibitor ameliorates progression of renal damage". Kidney International, vol. 68, 2005, pp. 2131-2142.
Schiweck et al., "Sugar Alcohols". Ullmann's Encyclopedia of Industrial Chemistry, Wiley-VCH Verlag GmbH & Co. KGaA, Weinheim, 2012, pp. 1-37.
Snively et al., "Chronic Kidney Disease: Prevention and Treatment of Common Complications". American Family Physicians, vol. 70, No. 10, Nov. 2004m pp. 1921-1928.
Stebbins et al., "Spinal angiotensin II influences reflex cardiovascular responses to muscle contraction". American Journal of Physiology, vol. 269, No. 4, Part 2, 1995pp. R864-R868.
Suga et al., "Angiotensin II type 1 receptor blockade ameliorates tubulointerstitial injury induced by chronic potassium deficiency". 2002, Kidney International, vol. 61, pp. 951-958.
Tran et al., "Modulation of microenvironmental pH and crystallinity of ionizable telmisartan using alkalizers in solid dispersions for controlled release". Journal of Controlled Release, vol. 129, No. 1, 2008, pp. 59-65.
Villar et al., "Ibuprofen, Aspirin and Acetaminophen Toxicosis and Treatment in Dogs and Cats". Veterinary Human Toxicology, vol. 40, No. 3, 1998, pp. 156-162.
Web site: www.merck.com "Chronic Kidney Disease," accessed on Dec. 13, 2010.
Web site: www.merck.com "Tubulointerstitial Nephritis," accessed on Jun. 1, 2009.
White, et al., "Effects of the angiotensin II receptor blockers telmisartan versus valsartan on the circadian variation of blood pressure: impact on the early morning period," Amer Journal of Hypertension, vol. 17, Issue 4, 2004, pp. 347-353.
Written Opinion of the International Searching Authority for PCT/EP2010/056895 dated Aug. 3, 2010.
Xiao et al., "Regional Hemodynamic Effects of the AT1 Receptor Antagonist CV-11974 in Conscious Renal Hypertensive Rats". Hypertension, vol. 26, 1995, pp. 989-997.
Polzin et al., "Treating Feline Kidney Disease: An Evidence-Baed Approach". North American Veterinary Conference Proceedings, Jan. 7, 2006, pp. 1-6. [Accessed at http://www.iknowledgenow.com/article.cfm?documentID=2817&transactionKey . . . on Dec. 16, 2014].

(56) References Cited

OTHER PUBLICATIONS

Lim et al., "Angiotensin II Blockade Reverses Myocardial Fibrosis in a Transgenic Mouse Model of Human Hypertrophic Cardiomyopathy". Circulation, vol. 103, Feb. 2001, pp. 789-791. [Accessed at http://circ.ahaqjournals.org/ on Sep. 3, 2014].

Li et al., "Efficacy evaluation of Telmisartan in treatment of dilated cardiomyopathy with heart failure". Chinese Heart Journal, vol. 18, No. 4, 2006, pp. 427-429.

Norikazu et al., "Comparison of angiotensin II receptor antagonists and angiotensin converting enzyme inhibitors on a dog suffering mild mitral insufficiency". Annual Meeting of the Japanese Society of Veterinary Science, vol. 137, 2004, p. 104.

Wienen et al., "A Review on Telmisartan: A Novel, Long-Acting Angiotensin II-Receptor Antagonist". Cardiovascular Drug Reviews, vol. 18, No. 2, 2000, pp. 127-154.

Xue, Jintong. "Chapter 13. Hypertensive Disease". Practical Handbook for the Diagnosis and Treatment of Cardiovascular Disease, First Edition, Zhengzhou University Press, 2005, pp. 480-508.

Jensen et al., "Plasma renin activity and angiotensin I and aldosterone concentrations in cats with hypertension associated with chronic renal disease." American Journal of Veterinary Research, vol. 58, No. 5, May 1997, pp. 535-540.

Buoncompagni et al., "Treatment of Systemic Hypertension Associated With Kidney Disease." Compendium: Continuing Education for Veterinarians, Vetleam.com, 2013, pp. E1-E6.

Honjo et al., "Possible Beneficial Effect of Telmisartan on Glycemic Control in Diabetic Subjects". Diabetes Care, vol. 28, No. 2, Fe. 2005, p. 498.

Pershadsingh et al., "Insulin-Sensitizing Effects of Telmisartan". Diabetes Care, vol. 27, No. 4, Apr. 2004, p. 1015.

Yoshida et al., "Metabolic effect of AII receptor antagonists." Ketsuatsu (Blood Pressure), vol. 9, No. 8, 2002, pp. 802-806. (Abstract in English).

Ebner et al., "In vitro flucuronidation of the angiontensin II receptor antagonist telmisartan in the cat: a comparison with other species." Journal of Vetrinary Pharmacology and Therapeutics, vol. 36, 2012, pp. 154-160.

Maruo et al., "Polymorphism of UDP-Glucuronosyltransferase and Drug Metabolism." Current Drug Metabolism, vol. 6, 2005, pp. 91-99.

Adamson et al., "The Fate of Sulphadimethoxine in Primates Compared with other Species". Biochemical Journal, vol. 118, 1970, pp. 41-45.

Caldwell et al., "Species Differences in Xenobiotic Conjugation". Xenobiotic Metabolism and Disposition, Proceedings of the 2nd International ISSX Meeting, Kobe, Japan, May 16-20, 1988, pp. 217-224.

Caldwell et al., "Drug Metabolism in 'Exotic' Animals". European Journal of Drug Metabolism and Pharmacokinetics, No. 2, 1978, pp. 61-66.

Court et al., "Molecular genetic basis for deficient acetaminophen glucuronidation by cats: UGT1A6 is a pseudogene, and evidence for reduced diversity of expressed hepatic UGT1A isoforms". Pharmacogenetics, vol. 10, 2000, pp. 355-369.

Harley et al., "Proteinuria in dogs and cats." Canadian Veterinary Journal, vol. 53, Jun. 2012, pp. 631-638.

\* cited by examiner

ORAL SUSPENSION COMPRISING TELMISARTAN

RELATED APPLICATIONS

This application is a continuation of U.S. patent application Ser. No. 13/321,216, filed Dec. 19, 2011, which is a national stage entry of international patent application PCT/EP2010/056895, which was filed May 19, 2010, and to European Patent Application No. EP 09160771.3, which was filed May 20, 2009. The teachings and contents of which are incorporated herein by reference in their entirety. All applications are commonly owned.

FIELD OF THE INVENTION

The present invention relates to a pharmaceutical solution, preferably a drinkable pharmaceutical solution with a pH of 10 or more containing an angiotensin-II-receptor antagonist, preferably the active substance telmisartan, as well as one or more sugar alcohols added in order to improve flavour and shelf life, wherein the content of reducing sugars before the addition of the sugar alcohol or alcohols to the solution does not exceed 1000 ppm.

BACKGROUND TO THE INVENTION

Telmisartan, the INN name of the compound 4'-((2-n-propyl-4-methyl-6-(1-methylbenz-imidazol-2-yl)-benzimidazol-1-yl)methyl)biphenyl-2-carboxylic acid (IUPAC) having the following formula

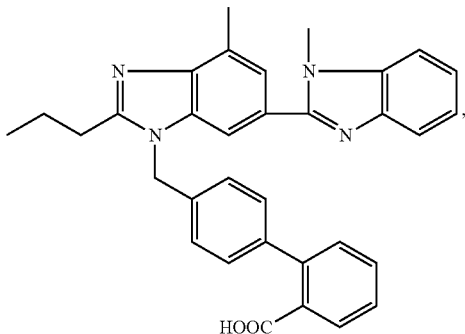 [SMILES: CCCc1nc2c(C)cc(-c3nc4ccccc4n3C)cc2n1Cc1ccc(-c2ccccc2C(=O)O)cc1]

is an angiotensin-II-receptor antagonist, which is licensed for the treatment of hypertension and is available in tablet form in different dosage strengths. For use in children, particularly children under 6 years old, and in older or sick people with difficulty swallowing, it is often not possible to use tablets as a medical formulation. In domestic pets such as dogs and cats it would theoretically be possible to administer tablets, but often the tablets are held in the animal's cheek pouches and spat out again later, thus seriously impairing the dosage reliability. In addition, it is only possible to adapt dosage to weight to a limited extent, owing to the given fixed dosage steps of the tablets.

More suitable, and preferable from a physiological point of view, is a drinkable solution, free from organic cosolvents, which may be administered in controlled amounts using suitable calibrated dosing aids such as dosage sprays, pipettes, spoons or cups. There is also the possibility of making the formulation more acceptable to children and even pets by the addition of flavour improvers, which is advantageous particularly for long-term administration for treating hypertension.

SUMMARY AND DESCRIPTION OF THE INVENTION

The aim of the present invention is to provide a pharmaceutical solution, preferably a drinkable pharmaceutical solution containing an angiotensin-II-receptor antagonist. Preferred angiotensin II receptor antagonists are the substances known by the following INN names: candesartan, eprosartan, irbesartan, losartan, olmesartan, tasosartan, telmisartan and valsartan, and the pharmaceutically acceptable salts, hydrates or polymorphs thereof. The concentration of the angiotensin-II-receptor antagonist, preferably telmisartan, needed in the solution in order to achieve therapeutic doses should be between 1 mg/ml and 10 mg/ml. Moreover, because of the strongly pH-dependent solubility profile of telmisartan an aqueous formulation should have a pH that is either less than 2 or more than 10, in order to ensure a physically stable solution.

Based on these requirements, attempts were made first of all to provide a formulation in the acid pH range, as significantly more preservatives are available for this pH range, if needed (the use of multi-dose containers for this intended application is clearly preferable).

The following main ingredients of the formulation were used:
  a) pH-active components for ensuring solubility in the desired concentration range;
  b) flavour-correcting components (sugars, sugar alcohols, sugar substitutes, flavour additives) to mask the bitter, rasping taste of telmisartan;
  c) texture enhancers, usually viscosity-increasing adjuvants such as for example cellulose derivatives, PVP, glycerol;
  d) preservatives for ensuring microbiological quality in the multi-dose container; and optionally
  e) antioxidants such as for example BHA, BHT, EDTA or propylgallate for stabilising the formulation.

During this development work it was found that for concentrations of active substance greater than 1 mg/ml a pH of less than 1.5 is needed, which requires the use of strong organic acids such as for example methanesulphonic acid or phosphoric acid. The very powerfully astringent effect of such acidic solutions makes acidic formulations of this kind totally unsuitable for long-term use particularly in children but also in domestic pets such as dogs and cats.

Further development work therefore had to be shifted to the pH range ≥10. The base components used for this work were first of all sodium hydroxide solution, meglumine or a combination of sodium hydroxide solution and meglumine, in order to produce a physically and chemically stable solution. The use of alkali metal or alkaline earth metal carbonates/-hydrogen carbonates does not produce a sufficiently high pH in the present instance. The use of ethanolamines was also ruled out in view of the administration route and target group.

For masking or improving the bitter, rasping taste of telmisartan in solution, besides conventional quantities of synthetic sugar substitutes (saccharine, saccharine-Na, Na-cyclamate, acesulfame, aspartame, sucralose etc.), which have a risk of intolerance or in some cases are not internationally permitted (Na-cyclamate), sugar alcohols such as for example xylitol, maltitol, sorbitol, or mannitol were investigated for their suitability. They are not cariogenic (converted slowly into the acid) and have a low calorific value, which is a major advantage for long-term use particularly in children but also in pets. Although they are suitable in principle, the use of the normal sugars (glucose, glucose syrup, fructose, saccharose, maltose, lactose etc.) is avoided because of the disadvantages mentioned above (e.g. cause of tooth decay, calorie loading).

Against the background of the target groups and long-term administration the addition of flavourings was largely avoided because of the potential for allergies, although it is theoretically possible to add a substance without affecting the properties of the telmisartan solution according to the invention. Examples of such flavourings are cherry, strawberry, raspberry, tutti-frutti, currant, caramel, chocolate and mint flavourings, as well as meat and fish flavourings for animals.

In order to improve the subjective overall impression of the telmisartan solution according to the invention (fullness/consistency/viscosity/texture) it is also possible to use glycerol as well as cellulose derivatives such as hydroxyethylcellulose, hydroxypropylcellulose, methylcellulose or hydroxypropylmethylcellulose; or soluble PVP in small concentrations. Their use is not necessary but is useful for prolonging the contact times before the taste receptors are reached, and thereby further masking the bitter flavour.

There are only a very few preservatives available in suitable concentrations for the pH range of 10 and above: thus, apart from the phenol derivatives such as e.g. the cresols, which are used predominantly parenterally in the field of insulin formulations, only the quaternary ammonium compounds are available. Their toxicity must be viewed critically with regard to the target groups and long-term administration. Thus, basically, the only sufficiently acceptable option available is benzalkonium chloride, but its orally unpleasant bitter flavour represents an additional problem. Therefore investigations were carried out first of all to determine the degree to which the concentration of the sugar alcohols used was able to meet the requirements of the Pharmacopoeia regarding the Preservation Loading Test (PLT) summarised in the following Table 1.

TABLE 1

Required reduction in number of microbes in log PFU per test microbe
Preservation loading test according to USP or Ph. Eur.

|  | after 14 days' incubation | | after 28 days' incubation | |
| --- | --- | --- | --- | --- |
|  | USP | Ph. Eur. | USP | Ph. Eur. |
| Bacteria* | 1 | 3 | no increase | no increase |
| Fungi** | no increase | 1 | no increase | no increase |

*E. coli, S. aureus, P. aeruginosa
**C. albicans, A. niger

Because of their sweetening power and taste similarity to glucose in terms of sweet sensation the sugar alcohols xylitol, maltitol, sorbitol and mannitol are particularly preferred. Maltitol is particularly preferred. However, identical results in terms of preserving effect can also be obtained with the other sugar alcohols. Surprisingly it has been found that above a sugar alcohol concentration of at least 60% (percent by weight/volume) in a drinkable aqueous telmisartan solution the requirements of the USP Pharmacopoeia in a preservative load are met, but the enhanced requirements of the European Pharmacopoeia are not. The criteria of the USP Preservation Loading Test are met less reliably as the concentration of active substance increases, but can be demonstrated up to an active concentration of 4 mg/ml.

Surprisingly it has now been found that reliably meeting the criteria of the USP Preservation Loading Test and also the concentration of telmisartan and the sugar alcohol concentration are dependent on the quality of the sugar alcohol or alcohols used. Of particular importance is the quantity of reducing sugars present. A content of up to 0.2% is permitted according to the Pharmacopoeia monograph. Within the scope of our investigations it has become apparent that to ensure that the USP Preservation Loading Test is safely complied with the content of reducing sugar (primarily maltose and glucose) in the sugar alcohol, i.e. the quantity of reducing sugars in the sugar alcohol should not exceed 1000 ppm, best of all should not exceed 300 ppm, before the addition.

The threshold value of less than 300 ppm of reducing sugar in the maltitol corresponds to less than 300 mg of reducing sugar per kg of maltitol, or less than 0.3 mg of reducing sugar per gram (g) of maltitol.

A 60% sugar alcohol solution (i.e. 60 g sugar alcohol per 100 ml of solution) thus should contain at most 18 mg of reducing sugar per 100 ml or 0.18 mg reducing sugar per ml of drinkable solution.

The threshold value represents, for example, for a
   40% sugar alcohol solution less than 0.12 mg reducing sugar per ml of drinkable solution;
   50% sugar alcohol solution less than 0.15 mg reducing sugar per ml of drinkable solution;
   60% sugar alcohol solution less than 0.18 mg reducing sugar per ml of drinkable solution; or for a
   70% sugar alcohol solution less than 0.21 mg reducing sugar per ml of drinkable solution Based on the amount of active substance of the angiotensin II receptor antagonist, preferably telmisartan, the content of reducing sugars should be less than 20 percent by weight, preferably less than 10 percent by weight and particularly preferably less than 5 percent by weight.

It has thus been shown that the stability of a drinkable telmisartan solution is dependent on the amount of reducing sugar contained in the sugar alcohol. The stability of a drinkable telmisartan solution deteriorates as the content of reducing sugars increases. Acidic breakdown products are formed resulting in a drop in the pH within the solution, which finally leads to the precipitation of the telmisartan as soon as the pH falls below 9.5/9.0. To obtain a telmisartan solution which is stable on storage, it is essential to add sugar alcohols such as e.g. xylitol, sorbitol or maltitol, provided that the amount of reducing sugars in the sugar alcohol of an aqueous drinkable telmisartan solution with a pH of ≥10 or higher is limited to below the content of sugar alcohols specified according to the Pharmacopoeia. A threshold value of 300 ppm or less is preferred. A correspondingly prepared aqueous drinkable telmisartan solution is stable for long periods. It thus has a storage stability of at least 12 months at 25° C./60% RH (relative humidity) and 30° C./70% RH, preferably at least 36 months at 25° C./60% RH and 30° C./70% RH. However it has also been found that a quantity of reducing sugars of at least 250 ppm has a positive effect on the stability of the active substance. Consequently, a content of a maximum content of 1000 ppm, preferably between 300 ppm and 250 ppm, of reducing sugars in the pharmaceutical solution is to be regarded as being preferred.

A drinkable telmisartan solution prepared using a sugar alcohol with a content of reducing sugar of 300 ppm or less does not require any antioxidants or stabilisers, and their addition is thus optional.

As the exclusive use of one or more sugar alcohols meets only the USP requirement for adequate preservation, the addition of benzalkonium chloride as a preservative was investigated by way of example for international licensing. The target was to add the smallest possible amount to meet the criteria, in accordance with the requirements laid down by the Pharmacopoeias. It was demonstrated that aqueous drinkable telmisartan solutions in a range of concentrations from 1-10 mg/ml, preferably 1-5 mg/ml, with a pH value of ≥10 or higher, a content of sugar alcohol of 40 percent by weight/volume (% W/V) or more as well as other optional formulation adjuvants above a benzalkonium chloride concentration of 0.005% W/V or higher reliably meet the requirements of the Ph.Eur. as well, while reliably masking the bitter taste of the benzalkonium chloride. Thus on the one hand it is ensured that the requirements of the Ph.Eur. are met and on the other hand the physiological loading is reduced to a minimum.

PREPARATION PROCESS

The present invention also describes a process for preparing the drinkable telmisartan solution according to the invention containing 1-10 mg/ml telmisartan, preferably 1-5 mg/ml telmisartan. As far as possible this process also uses methods known from the literature for aqueous solutions to be taken orally.

The process is characterised in that a suitable amount of active substance, optionally in the form of a salt or hydrate, is combined with a molar excess of a physiologically acceptable base dissolved in water, in order to obtain a solution with a pH of ≥10. Further formulation adjuvants are optionally added, and the solution is made up with purified water to obtain a concentration range of 1-10 mg of active substance per milliliter of solution. It should be noted that the solution corresponds to the properties already mentioned, particularly that of the pH value of 10. Exemplary formulations are presented herein in Examples 1-8.

In one particular embodiment a consistency-providing component such as for example a cellulose derivative or PVP is pre-swollen in a given amount of purified water at ambient temperature, then heated to a temperature of 70-80° C. until fully dissolved and then adjusted to a pH of 10 by the addition of the physiologically acceptable base, while the temperature is maintained at 70-80° C. The active substance is then added, with stirring, until a concentration of 1-10 mg/ml is obtained, and the sugar alcohol containing an amount of less than 1000 ppm, preferably less than 300 ppm of reducing sugar is added and dissolved. After the addition and dissolving of the sugar alcohol the solution is cooled to room temperature. Other formulation adjuvants such as synthetic sugar substitutes, flavourings or preservatives are added at RT with stirring. Finally, the pH is restored to 10 using the physiologically acceptable base, before purified water is added to top up to the required weight/volume. Lastly, the solution can be filtered to eliminate particulate impurities, before being transferred into suitable glass or plastic bottles.

The drinkable telmisartan solution according to the invention exhibits high stability on storage, which is not limited either by physical instability or by breakdown reactions of the active substance, and in terms of the selected pH it is sufficiently well tolerated physiologically.

The drinkable telmisartan solution according to the invention will now be explained by means of the following Examples. The Examples serve only as an illustration and are not to be regarded as restrictive.

EXAMPLES

Example 1

| | |
|---|---|
| telmisartan | 0.2 g |
| NaOH 1N | 0.68 ml |
| maltitol* | 60.0 g |
| hydroxyethylcellulose | 0.1 g |
| purified water | ad 100 ml |
| pH | 10 |
| stability | |
| 25° C./60% RH | >12 (18?) months |
| 30° C./70% RH | >12 (18?) months |
| Complies with PLT** according to USP/Ph. Eur. | USP |

*≤300 ppm red. sugar,
**PLT = preservation loading test

Example 2

| | |
|---|---|
| telmisartan | 0.1 g |
| meglumine | 0.6 g |
| maltitol* | 50.0 g |
| saccharine-Na | 0.6 g |
| hydroxyethylcellulose | 0.1 g |
| purified water | ad 100 ml |
| pH | 10 |
| stability | |
| 25° C./60% RH | >12 months |
| 30° C./70% RH | >12 months |
| Complies with PLT** according to USP/Ph. Eur. | — |

*≤300 ppm red. sugar,
**PLT = preservation loading test

Example 3

| | |
|---|---|
| telmisartan | 4 mg/ml |
| NaOH 1N | 0.8 ml |
| maltitol* | 60.0 g |
| hydroxyethylcellulose | 0.1 g |
| benzalkonium chloride | 0.005% |
| purified water | ad 100 ml |
| pH | 10 |
| stability | |
| 25° C./60% RH | >24 months |
| 30° C./70% RH | >24 months |
| Complies with PLT** according to USP/Ph. Eur. | USP and Ph. Eur. |

*≤300 ppm red. sugar,
**PLT = preservation loading test

Example 4

| | |
|---|---|
| telmisartan | 0.40 kg/100 L |
| NaOH 1N | 0.8 kg/100 L |
| maltitol* | 60.0 kg/100 L |
| hydroxyethylcellulose | 0.10 kg/100 L |
| benzalkonium chloride | 0.01 kg/100 L % |
| purified water | ad 100 L |
| pH | 10 |
| stability | |
| 25° C./60% RH | >24 months |
| 30° C./70% RH | >24 months |
| Complies with PLT** according to USP/ Ph. Eur. | USP and Ph. Eur. |

*≤300 ppm red. sugar,
**PLT = preservation loading test

Example 5

| | |
|---|---|
| telmisartan | 0.1 g |
| meglumine | q.s. ad pH 10 |
| maltitol* | 70.0 g |
| collidone K 25 | 0.2 g |
| purified water | ad 100 ml |
| pH | 10 |
| stability | |
| 25° C./60% RH | >18 (12?) months |
| 30° C./70% RH | >18 (12?) months |
| Complies with PLT** according to USP/ Ph. Eur. | USP |

*≤300 ppm red. sugar,
**PLT = preservation loading test

Example 6

| | |
|---|---|
| telmisartan | 4 mg/ml |
| NaOH 1N | 0.8 ml |
| xylitol* | 60.0 g |
| hypromellose | 0.1 g |
| purified water | ad 100 ml |
| pH | 10 |
| stability | |
| 25° C./60% RH | >12 (18?) months |
| 30° C./70% RH | >12 (18?) months |
| Complies with PLT** according to USP/ Ph. Eur. | USP |

*≤300 ppm red. sugar,
**PLT = preservation loading test

Example 7

| | |
|---|---|
| telmisartan | 2 mg/ml |
| NaOH 1N | 0.68 ml |
| sorbitol | 60.0 g |
| hypromellose | 0.1 g |
| purified water | ad 100 ml |
| pH | 10 |
| stability | |
| 25° C./60% RH | >18 months |
| 30° C./70% RH | >18 months |
| Complies with PLT** according to USP/ Ph. Eur. | USP |

*≤300 ppm red. sugar,
**PLT = preservation loading test

Example 8

| | |
|---|---|
| telmisartan (5 mg/ml) | 0.5000 g |
| NaOH | 1.9000 g |
| maltitol* | 60.000 g |
| hydroxyethylcellulose | 0.1000 g |
| purified water | 59.1600 g |
| pH | 10 |
| stability | |
| 25° C./60% RH | >24 months |
| 30° C./70% RH | >24 months |
| Complies with PLT** according to USP/ Ph. Eur. | USP |

*≤300 ppm red. sugar,
**PLT = preservation loading test

What is claimed:

1. A drinkable pharmaceutical solution
    telmisartan or a pharmaceutically acceptable salt, hydrate or polymorph thereof, wherein telmisartan is present in a concentration of 1 mg/ml to 10 mg/ml within the drinkable pharmaceutical solution;
    sodium hydroxide;
    one or more sugar alcohols selected from the group consisting of maltitol, xylitol, sorbitol, and mannitol, wherein the one or more sugar alcohols have a total concentration of 40 wt. % to 70 wt. % within the drinkable pharmaceutical solution and a maximum content of 2000 ppm of reducing sugar before addition to the drinkable pharmaceutical solution; and
    one or more consistency-providing components selected from the group consisting of hydroxyethylcellulose, hydroxypropylcellulose, methylcellulose, hydroxypropylmethylcellulose, hypromellose, and polyvinylpyrrolidone (PVP);
    optionally saccharin-Na;
    optionally benzalkonium chloride; and
    water;
    wherein the drinkable pharmaceutical solution has a pH of 10.

2. The pharmaceutical solution of claim 1, wherein the telmisartan is present in a concentration of 10 mg/ml.

3. The pharmaceutical solution of claim 1, wherein the one or more sugar alcohols have a maximum content of 1000 ppm of reducing sugar before addition to the drinkable pharmaceutical solution.

4. A kit comprising a container and the drinkable pharmaceutical solution of claim 1.

5. The kit of claim 4, further comprising a dosing aid for the drinkable pharmaceutical solution.

6. The kit of claim 4, wherein the container is glass or plastic.

7. A method of preparing the pharmaceutical solution of claim 1, comprising:

dissolving telmisartan or a pharmaceutically acceptable salt, hydrate or polymorph thereof and the one or more sugar alcohols in water and NaOH so as to obtain a concentration of telmisartan in the solution of 1 mg/ml to 10 mg/ml and a pH of 10.

8. A method of treating hypertension or kidney disease comprising orally administering a drinkable pharmaceutical solution to a cat, the pharmaceutical solution comprising:

telmisartan or a pharmaceutically acceptable salt, hydrate or polymorph thereof, wherein telmisartan is present in a concentration of 1 mg/ml to 10 mg/ml within the drinkable pharmaceutical solution; and one or more sugar alcohols, wherein the one or more sugar alcohols have a total concentration of 40 wt. % to 70 wt. % within the drinkable pharmaceutical solution and a maximum content of 2000 ppm of reducing sugar before addition to the drinkable pharmaceutical solution;

wherein the drinkable pharmaceutical solution has a pH of 10.

9. The method of claim 8, wherein telmisartan is present in a concentration of 1 to 5 mg/ml within the drinkable pharmaceutical solution.

10. The method of claim 8, wherein the one or more sugar alcohols have a maximum content of 1000 ppm of reducing sugar before addition to the drinkable pharmaceutical solution.

11. A method of treating hypertension or kidney disease comprising orally administering the drinkable pharmaceutical solution of claim 1 to a cat.

* * * * *